United States Patent
Tanaka

(10) Patent No.: US 10,058,291 B2
(45) Date of Patent: Aug. 28, 2018

(54) RADIOGRAPHIC APPARATUS

(71) Applicant: SHIMADZU CORPORATION, Kyoto (JP)

(72) Inventor: Masahiro Tanaka, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 601 days.

(21) Appl. No.: 14/427,976

(22) PCT Filed: May 24, 2013

(86) PCT No.: PCT/JP2013/003314
§ 371 (c)(1),
(2) Date: Mar. 12, 2015

(87) PCT Pub. No.: WO2014/041725
PCT Pub. Date: Mar. 20, 2014

(65) Prior Publication Data
US 2015/0245803 A1    Sep. 3, 2015

(30) Foreign Application Priority Data
Sep. 13, 2012  (JP) ................................. 2012-201556

(51) Int. Cl.
*A61B 6/00*   (2006.01)
*A61B 6/04*   (2006.01)
(Continued)

(52) U.S. Cl.
CPC .......... *A61B 6/0457* (2013.01); *A61B 6/0407* (2013.01); *A61B 6/10* (2013.01);
(Continued)

(58) Field of Classification Search
CPC ........... G01N 23/203; G01N 2223/053; G01N 21/956; G01N 2223/051; G01N 2223/616;
(Continued)

(56) References Cited

U.S. PATENT DOCUMENTS

2005/0129172 A1* 6/2005 Mertelmeier ........ A61B 6/0414
378/37
2008/0075228 A1* 3/2008 Tasaki .................. A61B 6/4494
378/37

FOREIGN PATENT DOCUMENTS

| JP | 2002-291734 A | 10/2002 |
|---|---|---|
| JP | 2003-334186 A | 11/2003 |

(Continued)

OTHER PUBLICATIONS

International Search Report issued in International Application No. PCT/JP2013/003314 dated Jul. 9, 2013, with English Translation.

*Primary Examiner* — Hoon Song
(74) *Attorney, Agent, or Firm* — McDermott Will & Emery LLP

(57) ABSTRACT

Provided is a radiographic apparatus with safety and time-saved imaging upon inclination of a subject without pulling an external instrument by the subject. In the radiographic apparatus, a top board supporting the subject placed thereon is rotatable and liftable. The characteristic feature of the embodiment is to control a level of an intersection of the top board and a line connecting an X-ray tube to an FPD to be constant in association with operation of a top-board rotation controller. This achieves a constant level of a region of interest (a site to be imaged) of the subject regardless of rotation of the top board. Consequently, an invariable distance is obtainable between the subject and the external instrument on the floor, allowing suppression in pulling of the external instrument due to a vertical movement of the (Continued)

subject. As a result, provision of a radiographic apparatus with safety and time-saved imaging is obtainable.

12 Claims, 6 Drawing Sheets

(51) Int. Cl.
    *A61B 6/10*     (2006.01)
    *A61B 5/20*     (2006.01)

(52) U.S. Cl.
    CPC .......... *A61B 6/4429* (2013.01); *A61B 6/4476* (2013.01); *A61B 6/481* (2013.01); *A61B 5/20* (2013.01); *A61B 6/50* (2013.01); *A61B 6/545* (2013.01)

(58) Field of Classification Search
    CPC ...... G01V 5/0025; G01V 5/0066; G01V 5/12; A61B 6/483
    See application file for complete search history.

(56) References Cited

FOREIGN PATENT DOCUMENTS

| | | |
|---|---|---|
| JP | 2004-033420 A | 2/2004 |
| JP | 2004-121604 A | 4/2004 |
| JP | 2006-081785 A | 3/2006 |
| JP | 2010-012101 A | 1/2010 |
| JP | 2011-072343 A | 4/2011 |

\* cited by examiner

Fig. 8
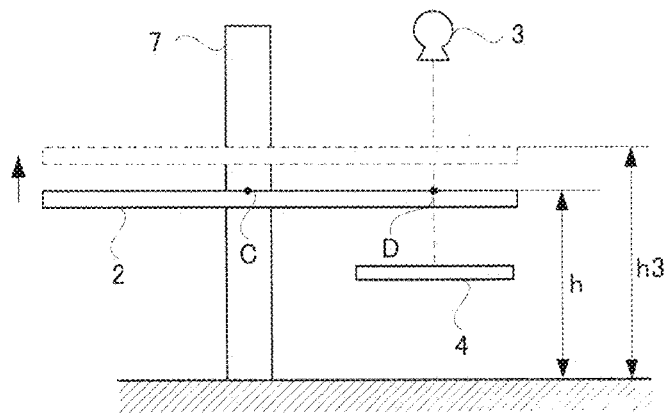
| ALIMENTARY SYSTEM INSPECTION | h1 |
| LUNG INSPECTION | h2 |
| URINARY ORGAN INSPECTION | h3 |
Fig. 9
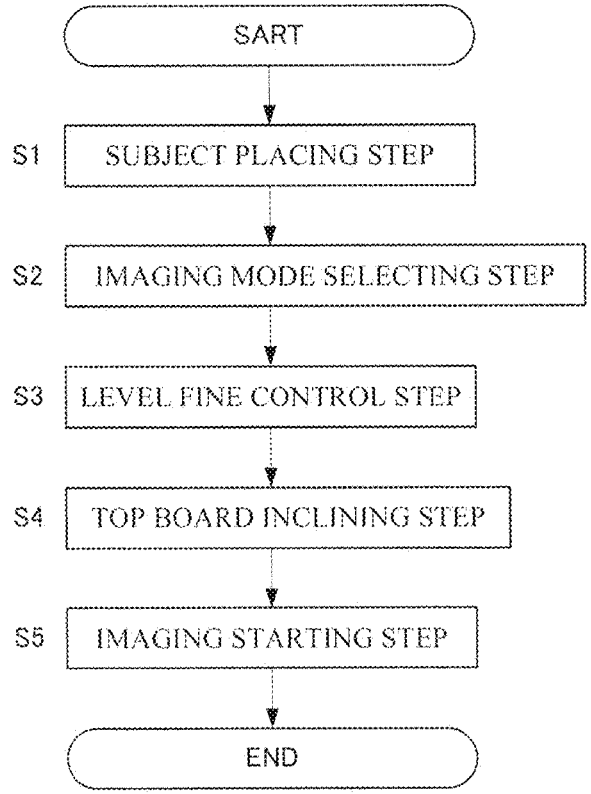
Fig. 10

Fig.11
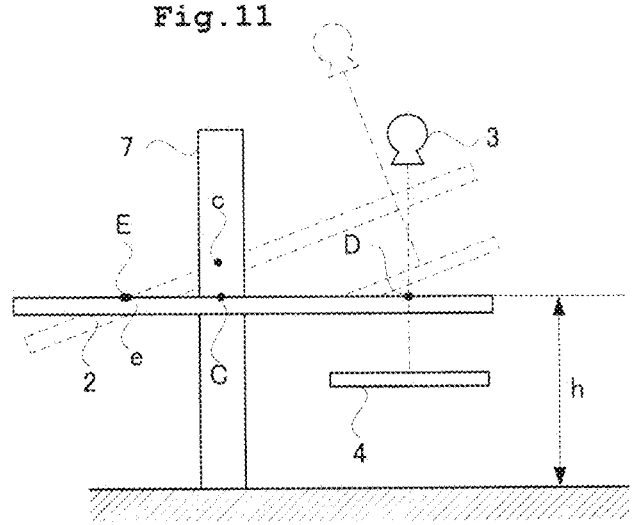
Fig.12
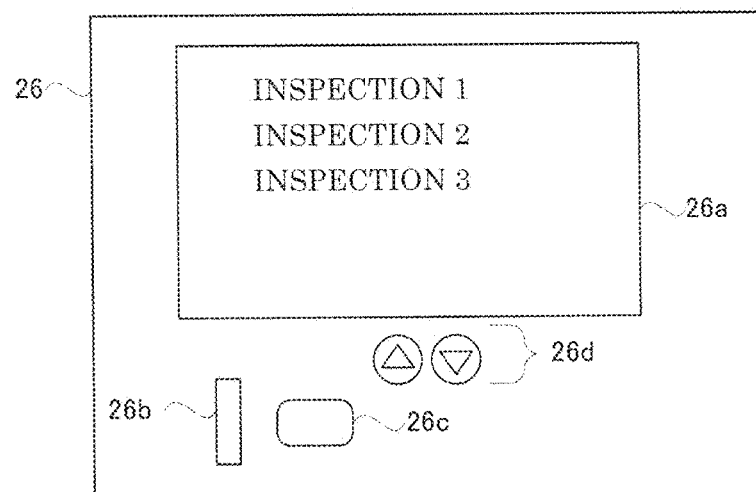
Fig.13
| INSPECTION 1 | E1 |
| --- | --- |
| INSPECTION 2 | E2 |
| INSPECTION 3 | E3 |
| | |
| | |

RADIOGRAPHIC APPARATUS

RELATED APPLICATIONS

This application is a national phase of International Application No. PCT/JP2013/003314, filed on May 24, 2013, which in turn claims the benefit of Japanese Application No. 2012-201556, filed on Sep. 13, 2012, the disclosures of which Applications are incorporated by reference herein.

TECHNICAL FIELD

The present invention relates to a radiographic apparatus that images a subject by emitting radiation to the subject. More particularly, the present invention is directed to a radiographic apparatus that allows inclination of a top board supporting a subject placed thereon.

BACKGROUND ART

Medical institutions are equipped with a radiographic apparatus configured to emit radiation to image a subject M. Such a radiographic apparatus includes a radiation source 53 and a detector 54 as illustrated in FIG. 14. The radiation source 53 emits radiation, and the detector 54 detects radiation. A top board 52 is provided between the radiation source 53 and the detector 54. The top board 52 supports the subject M placed thereon. See, for example, Japanese Patent Publication No. 2010-012101A.

Such a radiographic apparatus allows inclination of the top board 52. The top board 52 rotates around an axis C, whereby the subject M on the top board 52 is inclinable to a desired angle. See FIG. 15.

The top board 52 is rotated, and the radiation source 53 and the detector 54 rotate following the rotation with a maintained positional relationship to the top board 52. Consequently, the rotation of the top board 52 never changes the positional relationship among the subject M, the radiation source 53, and the detector 54. Such rotation achieves imaging while a direction where a liquid contrast medium administered into the subject M drips is adjusted.

Here, the radiation source 53 and the detector 54 are movable relative to the top board 52 in a long-side direction of the top board 52. In the currently-used apparatus, a positional relationship between the top board 52 and the center of the rotation is constant even when the above movement is made. This is because a positional relationship between the top board 52 and a rotating mechanism rotatably holding the top board 52 is constant regardless of the movement of the radiation source 53 and the detector 54.
Patent Literature 1: Japanese Patent Publication No. 2010-012101A

SUMMARY OF INVENTION

Technical Problem

However, the currently-used apparatus possesses the following drawback. That is, the currently-used apparatus has difficulty in imaging when a region of interest of the subject M is located at one end of the top board 52.

FIG. 16 illustrates an inspection for urinary organs using the currently-used radiographic apparatus. In such a case, the radiation source 53 and the detector 54 are moved to one end of the top board 52 so as for a urinary bladder and the like of the subject M falls within an imaging area.

When the top board 52 is rotated in such a manner for inclination of the subject M, one end of the top board 52 is moved upward in association with the rotation of the top board 52. That is, the subject M is lifted up in association with the rotation of the top board 52.

The lift-up of the subject M in association with the rotation of the top board 52 is not particularly problematic in the currently-used apparatus. This is because the radiation source 53 and the detector 54 also move upward along with the lift-up of the subject M, and thus a relative position among them is invariable. As noted above, imaging the same position of the subject M is obtainable regardless of the rotation of the top board 52. Consequently, with the currently-used apparatus, vertical movement of the subject M is considered not to affect the imaging.

In actual, however, the vertical movement of the subject M causes a variation in distance between the subject M and an external instrument, such as a holder for holding a contrast medium container, on the floor. A catheter for supplying a contrast medium to the subject M is needed for an inspection for urinary organs. Such a contrast medium is supplied from the contrast medium container via a tube into the subject, the container being filled with the contrast medium. The container is held by the holder on the floor.

When the subject M moves vertically with the catheter being inserted thereinto, the subject M pulls the contrast medium container through the tube. This may cause the holder holding the contrast medium container to topple over. In addition, when the subject M has to be subjected to an inspection while being put on a drip, the vertical movement of the subject M may also cause the holder holding the drip to topple over.

An operator has to pay attention during the inspection to avoid such events. Accordingly, the operator fails to focus on the imaging.

The present invention has been made regarding the state of the art noted above, and its one object is to provide a radiographic apparatus with safety and time-saved imaging upon inclination of a subject without pulling an external instrument by the subject.

Solution to Problem

The present invention adopts the following construction for overcoming the above drawback. One embodiment of the present invention discloses a radiographic apparatus. The radiographic apparatus includes (A) a radiation source emitting radiation; (B) a top board supporting a subject placed thereon; (C) a detecting device detecting radiation passing through the subject; (D) a rotating device rotating the top board, the radiation source, and the detecting device with a maintained relative positional relationship thereamong, and rotating around a rotary shaft extending in a short-side direction of the top board; (E) a rotation control device controlling the rotating device; (F) a lifting device moving the top board, the radiation source, and the detecting device rotated by the rotating device vertically with the maintained relative positional relationship; and (G1) a lifting controller controlling the lifting device in association with operation of the rotation control device so as for a level of an intersection of the top board and a line connecting the radiation source to the detecting device to be constant.

[Operation and Effect] In the radiographic apparatus according to the embodiment of the present invention, the top board supporting the subject placed thereon is rotatable and liftable. The characteristic feature of the embodiment of the present invention is to synchronize lifting and rotation of the top board. That is, the level of the intersection of the top board and the line connecting the radiation source to the detecting device is controlled to be constant in association with the operation of the rotation control device. This achieves a constant level of a region of interest (a site to be imaged) of the subject regardless of the rotation of the top board. Consequently, an invariable distance is obtainable between the subject and the external instrument on the floor, allowing suppression in pulling of the external instrument due to the vertical movement of the subject. As a result, the embodiment of the present invention allows provision of a radiographic apparatus with safety and time-saved imaging.

Moreover, the radiographic apparatus further includes an imaging-system moving device moving the radiation source and the detecting device integrally relative to the top board in a long-side direction of the top board, and an imaging-system movement controller controlling the imaging-system moving device. A positional relationship between the rotary shaft and the top board when the rotating device rotates the top board, the radiation source, and the detecting device is invariable regardless of operation of the imaging-system moving device. Such is more preferable.

[Operation and Effect] The above is a concrete construction of the present invention. That is, the construction in which the radiation source and the detecting device are moved integrally relative to the top board in the long-side direction of the top board achieves shifting of the area to be imaged on the top board in accordance with a target for inspection.

Moreover, the radiographic apparatus further includes (H) an input device inputting selection of operating or not operating the lifting controller in association with the rotation control device. Such is more preferable.

[Operation and Effect] The above is a concrete construction of the present invention. An operator inputs selection of operating or not operating the lifting controller in association with the rotation control device. This obtains imaging while a moving form of the top board according to the embodiment of the present invention with a maintained level of the intersection and a currently-used moving form of the top board are selectable freely. Consequently, the above construction allows provision of a radiographic apparatus with a high degree of flexibility for imaging.

Moreover, the radiographic apparatus further includes a storing device storing a table that links an intersection level as a positional set value of the intersection in the vertical direction with an imaging mode indicating an imaging target. The input device causes an operator to input the imaging mode in addition to the inputting selection. The lifting controller controls the lifting device, prior to the operation of the rotation control device, so as for the intersection to be shifted in the vertical direction to a level of the intersection associated with the imaging mode inputted via the input device by the operator. Such is more preferable.

[Operation and Effect] The above is a concrete construction of the present invention. As in the above construction in which the imaging mode indicating the imaging target is selectable, setting the level of the intersection is obtainable in association with the specified imaging mode by the operator. This achieves an automatic shift of the intersection to a level suitable for imaging by merely selecting the imaging mode. As a result, the above construction allows provision of a radiographic apparatus with ease of operation.

Moreover, in the radiographic apparatus with both the imaging-system moving device and the element (H), if a command is inputted via the input device to start association of the lifting controller, the lifting controller operates to maintain the level of the intersection to be constant. Such is more preferable.

[Operation and Effect] The above is a concrete construction of the present invention. The lifting controller maintains a level of the intersection when the command is input to start the association to be constant as noted above. This allows provision of a radiographic apparatus with ease of imaging. This is because the lifting controller never changes a portion of the top board maintaining a constant level even when the radiation source and the detecting device are moved relative to the top board to shift the intersection of the top board and the line connecting the radiation source to the detecting device.

Moreover, the radiographic apparatus according to the embodiment of the present invention is applicable to an inspection for urinary organs.

[Operation and Effect] The above is a concrete construction of the present invention. The radiographic apparatus according to the embodiment of the present invention is suitable for an inspection for urinary organs. Upon the inspection for urinary organs, the region of interest of the subject is located at one end of the top board in the long-side direction. Accordingly, rotation of the top board is likely to cause a variation in distance between the floor and the region of interest of the subject. The embodiment of the present invention achieves a constant level of the region of interest of the subject. Consequently, a possibly suppressed variation in positional relationship between the subject and the external instrument is obtainable, and thus a radiographic apparatus with ease for operation can be provided.

Moreover, another embodiment of the present invention discloses a radiographic apparatus including (A) a radiation source emitting radiation; (B) a top board supporting a subject placed thereon; (C) a detecting device detecting radiation passing through the subject; (D) a rotating device rotating the top board, the radiation source, and the detecting device with a maintained relative positional relationship thereamong, and rotating around a rotary shaft extending in a short-side direction of the top board; (E) a rotation control device controlling the rotating device; (F) a lifting device moving the top board, the radiation source, and the detecting device rotated by the rotating device vertically with the maintained relative positional relationship; and (G2) a lifting controller controlling the lifting device in association with operation of the rotation control device so as for a level of a portion on the top board to be maintained constant.

[Operation and Effect] The above is another aspect of the construction that the present invention is adoptable. That is, in the apparatus having the above element (G1), the intersection of the top board and the line connecting the radiation source to the detecting device is a target whose level is maintained constant. Instead of the construction, a level of any position on the top board as the element (G2) may be maintained constant. This also can obtain the same effect as that mentioned in the above embodiment. Any construction is adoptable depending on the imaging target by the radiographic apparatus.

Moreover, the radiographic apparatus with the above element (G2) further includes an input device inputting selection of the portion on the top board. Such is more preferable.

[Operation and Effect] The above is a concrete construction of the present invention. The input device inputting selection of the portion on the top board ensures an operator setting of a desired position on the top board to be maintained constant in level.

Moreover, the radiographic apparatus with the above element (G2) further includes a storing device storing a table linking the position of the portion on the top board with the imaging mode indicating the imaging target, and an input device causing the operator to select the imaging mode. Such is more preferable.

[Operation and Effect] The above is a concrete construction of the present invention. With the above construction in which the imaging mode indicating the imaging target is selectable, the position on the top board to be maintained constant in level is set in associated with the specified imaging mode by the operator. This achieves automatic determination of a portion on the top board to be maintained in level by merely selecting the imaging mode. Consequently, the above construction allows provision of a radiographic apparatus with more ease for operation.

Moreover, the radiographic apparatus with the above element (G2) is applicable to an inspection for myeloma.

Advantageous Effects of Invention

In the radiographic apparatus according to the embodiment of the present invention, the top board supporting the subject placed thereon is rotatable and liftable. The characteristic feature of the embodiment of the present invention is to synchronize lifting and rotation of the top board. That is, the level of the intersection of the top board and the line connecting the radiation source to the detecting device is controlled to be constant in association with the operation of the rotation control device. This achieves a constant level of a region of interest (a site to be imaged) of the subject regardless of the rotation of the top board. Consequently, an invariable distance is obtainable between the subject and the external instrument on the floor, allowing suppression in pulling of the external instrument due to the vertical movement of the subject. As a result, the embodiment of the present invention allows provision of a radiographic apparatus with safety and time-saved imaging.

BRIEF DESCRIPTION OF DRAWINGS

FIG. 8 is a schematic view illustrating a table according to the embodiment.

FIG. 9 is a schematic view illustrating fine control in level of a top board according to the embodiment.

FIG. 10 is a flow chart illustrating operation of the X-ray apparatus according to the embodiment.

FIGS. 11 to 13 are schematic views each illustrating one modification of the present invention.

DESCRIPTION OF EMBODIMENTS

The following describes embodiments for carrying out the present invention.

Embodiment 1

One embodiment of the present invention is to be described hereinunder. X-rays in the embodiment correspond to radiation in the present invention. An FPD is the abbreviation of a flat panel detector. The X-ray apparatus 1 according to the embodiment of the present invention is especially used for an inspection for urinary organs.

<Whole Construction of X-Ray Apparatus>

Figure 1:
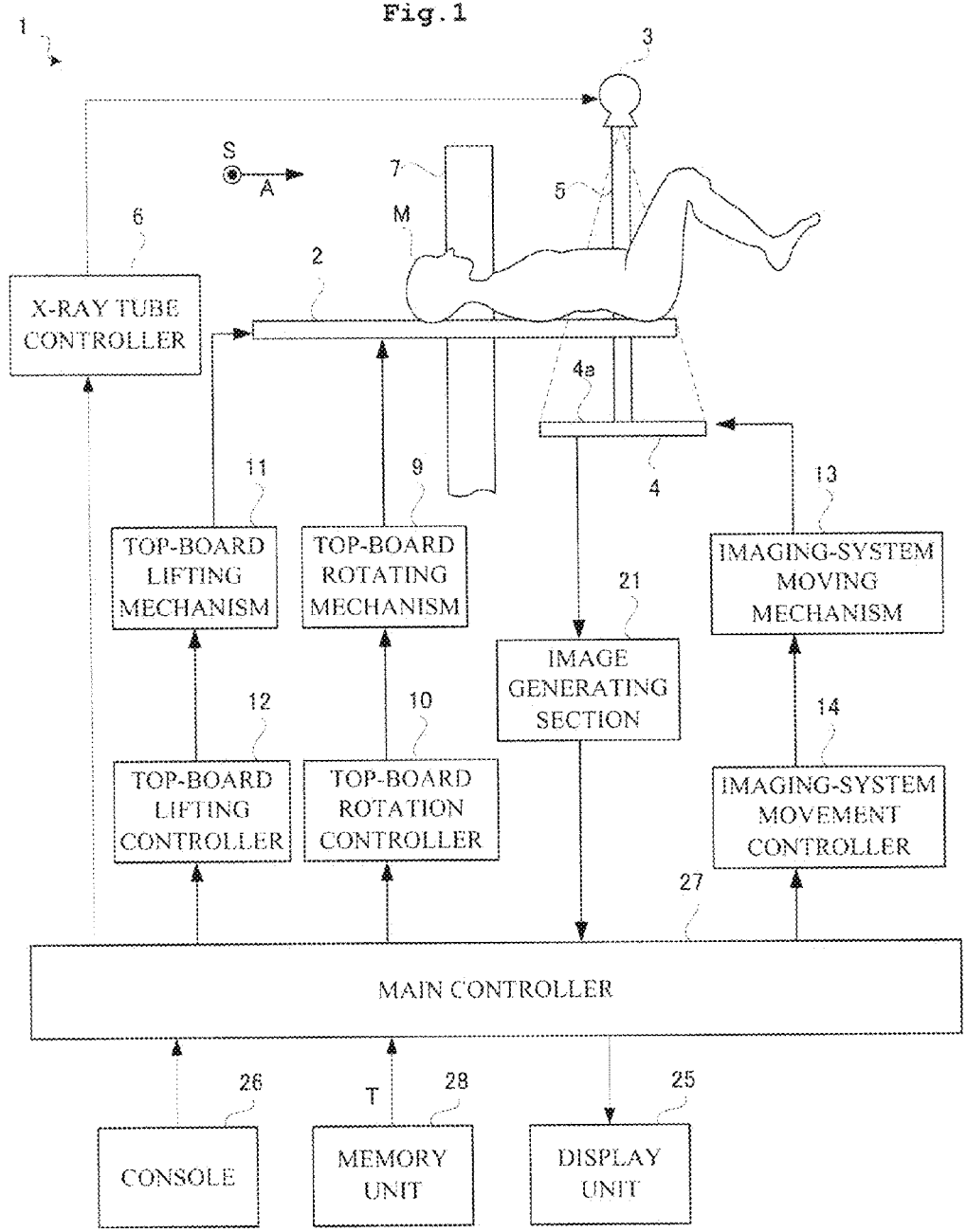
FIG. 1 is a function block diagram illustrating a whole X-ray apparatus according to one embodiment of the present invention.

Firstly, an X-ray apparatus 1 according to Embodiment 1 is to be described. As illustrated in FIG. 1, the X-ray apparatus 1 includes a top board 2 that supports a subject M placed thereon in a supine position, an X-ray tube 3 above the top board 2 that emits X-rays, and a FPD 4 below the top board 2 that detects X-rays passing through the subject M. The FPD 4 is rectangular having four sides along either a body axis direction A or a body side direction S of the subject M. The X-ray tube 3 emits X-ray beams radially spreading in a quadrangular pyramid shape to the FPD 4. An entire surface of the FPD 4 receives X-ray beams. The detecting surface 4a of the FPD 4 for detecting X-rays includes X-ray detecting elements arranged two-dimensionally in the body axis direction A and the body side direction S. Here, the X-ray tube 3 corresponds to the radiation source in the present invention. The FPD 4 corresponds to the radiation detecting device in the present invention.

Figure 2:
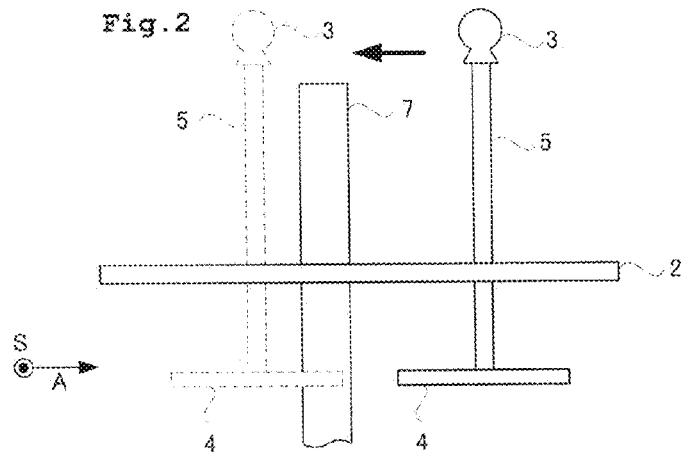
FIG. 2 is a schematic view illustrating operation of an imaging-system moving mechanism according to the embodiment.

A strut 5 supports imaging systems 3 and 4 composed of the X-ray tube 3 and FPD 4, respectively. The strut 5 is driven by an imaging-system moving mechanism 13. The strut 5 is movable relative to the top board 2 in the body axis direction A of the subject M. In this manner, the imaging-system moving mechanism 13 moves the X-ray tube 3 and the FPD 4 integrally relative to the top board 2 in a long-side direction of the top board 2. Such movement allows change of a position where radiography is conducted to the subject M. An imaging-system movement controller 14 controls the imaging-system moving mechanism 13. As illustrated in FIG. 2, the imaging-system moving mechanism 13 moves the imaging systems 3 and 4 together with the strut 5. Consequently, moving the imaging-system moving mechanism 13 causes no variation in positional relationship among the X-ray tube 3, the FPD 4, and the strut 5. The imaging-system moving mechanism 13 corresponds to the imaging-system moving device in the present invention. The imaging-system movement controller 14 corresponds to the imaging-system movement controller in the present invention.

A top board holder 7 extends vertically from the floor of an inspection room. The top board holder 7 holds the top board 2 rotatably and liftably. The following firstly describes how the top board holder 7 holds the top board 2 rotatably. A top-board rotating mechanism 9 provided in the top board holder 7 rotates the top board 2. A top-board rotation controller 10 controls the top-board rotating mechanism 9. The top-board rotating mechanism 9 corresponds to the rotating device in the present invention. The top-board rotation controller 10 corresponds to the rotation control device in the present invention.

Figure 3:
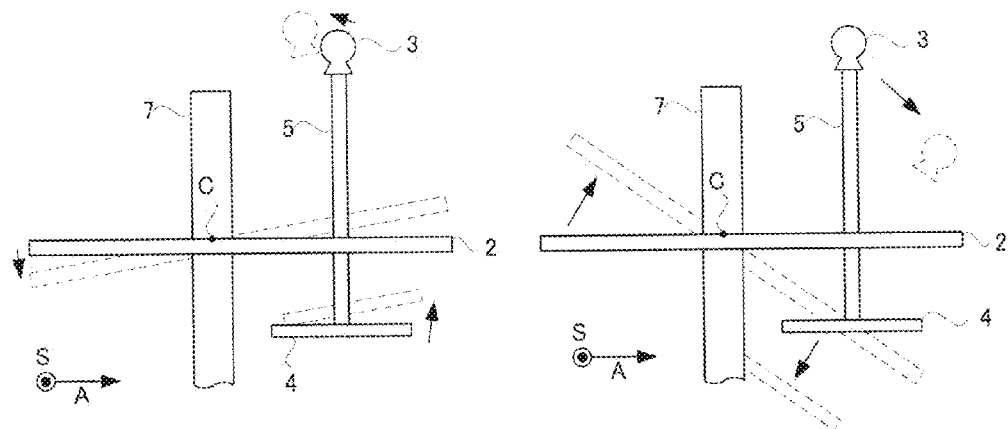
FIG. 3 is a schematic view illustrating operation of a top-board rotating mechanism according to the embodiment.

FIG. 3 illustrates how the top-board rotating mechanism 9 rotates the top board 2. FIG. 3 illustrates on the left thereof how the top board 2 is rotated counterclockwise around an axis C located at an intersection of the top board 2 and the top board holder 7. FIG. 3 illustrates on the right thereof how the top board 2 is rotated clockwise around the axis C. Here, the axis C extends in a short-side direction of the top board 2 (body side direction S of the subject M).

It should be noted in FIG. 3 that the imaging systems 3 and 4 are rotated following the rotation of the top board 2. That is, the top-board rotating mechanism 9 holds not only the top board 2 but also the strut 5 and the imaging-system moving mechanism 13 integrally. Accordingly, the rotation of the top board 2 causes the strut 5 to be rotated with a maintained relative positional relationship between the strut 5 and the top board 2. Consequently, the imaging systems 3 and 4 are also rotated following the rotation of the top board 2 with a maintained relative positional relationship to the top board 2. In this manner, the top-board rotating mechanism 9 rotates the top board 2, the X-ray tube 3, and the FPD 4 around the axis C extending in the short-side direction of the top board 2 with a maintained relative positional relationship among the elements. Here, a positional relationship between the axis C and the top board 2 is invariable depending on operation of the imaging-system moving mechanism 13. That is, the imaging-system moving mechanism 13 changes no positional relationship between the top-board rotating mechanism 9 and the top board 2.

The following describes how the top board holder 7 holds the top board 2 liftably. A top-board lifting mechanism 11 provided in the top board holder 7 lifts the top board 2. A top-board lifting controller 12 controls the top-board lifting mechanism 11. Here, the top-board lifting mechanism 11 corresponds to the lifting device in the present invention. The top-board lifting controller 12 corresponds to the lifting controller in the present invention.

Figure 4:
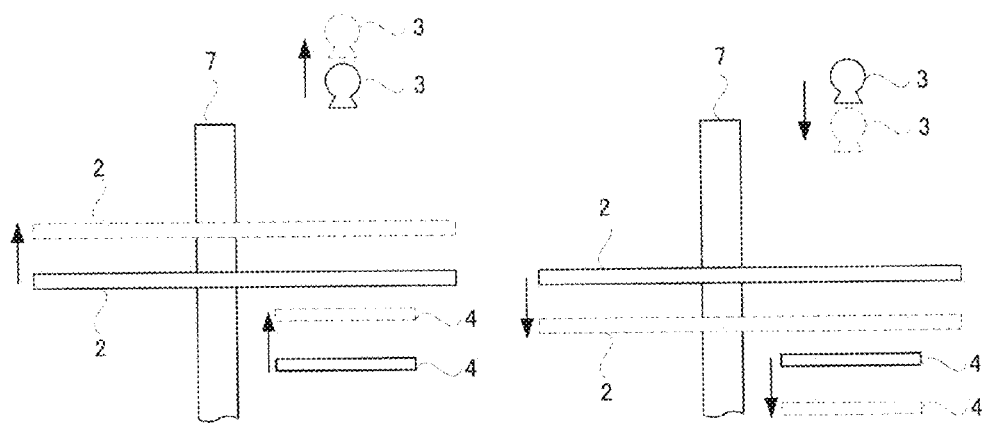
FIGS. 4 to 6 are schematic views each illustrating operation of a top-board lifting mechanism according to the embodiment.

FIG. 4 illustrates how the top-board lifting mechanism 11 lifts the top board 2. FIG. 4 illustrates on the left thereof how the top board 2 is moved upward vertically by vertical expansion of the top-board lifting mechanism 11 provided in the top board holder 7. FIG. 4 illustrates on the right thereof how the top board 2 is moved downward vertically by vertical contraction of the top-board lifting mechanism 11 provided in the top board holder 7.

It should be noted in FIG. 4 that the imaging systems 3 and 4 are also lifted following lifting of the top board 2. That is, the top-board lifting mechanism 11 holds not only the top board 2 but also the strut 5, the imaging-system moving mechanism 13, and the top-board rotating mechanism 9 integrally. Lifting the top board 2 causes the strut 5 to be lifted with a maintained relative positional relationship between the strut 5 and the top board 2. Accordingly, the imaging systems 3 and 4 are lifted following the lifting of the top board 2 with a maintained relative positional relationship to the top board 2. In this manner, the top-board lifting mechanism 11 moves the top board 2 rotated by the top-board rotating mechanism 9, the X-ray tube 3, and the FPD 4 vertically with a maintained positional relationship among the elements is maintained.

Such a relative positional relationship between the top board 2 and the imaging systems 3 and 4 is maintained invariable even when the top board 2 is moved while being rotated and lifted. The relative positional relationship between the top board 2 and the imaging systems 3 and 4 is variable by the imaging-system moving mechanism 13, and thus invariable by the top-board rotating mechanism 9 and the top-board lifting mechanism 11.

<Operation of Top-Board Lifting Controller>

Figure 5:
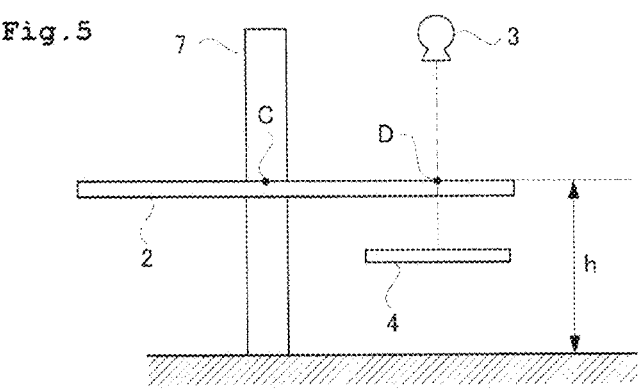

The following describes operation of the top-board lifting controller 12, which is the most characteristic in the present invention. FIG. 5 illustrates an initial condition of the top board 2 parallel to the floor of the inspection room. The initial condition is prior to rotation of the top board 2. Now an operator is to issue a command to rotate the top board 2 via a console 26. Then, the top-board rotating mechanism 9 rotates the top board 2 around the axis C, whereby the top board 2 starts rotation around the axis C. Here, the console 26 corresponds to the input device in the present invention.

The characteristic feature of the present invention is that the top-board lifting controller 12 operates following the rotation of the top board 2. That is, the top-board lifting controller 12 controls the top-board lifting mechanism 11 in association with the operation of the top-board rotating mechanism 9, whereby a level of an intersection D of a focus of the X-ray tube 3 and the center of the FPD 4 is maintained constant. Consequently, a distance between the intersection D and the floor of the inspection room is always constant regardless of the rotation of the top board 2. Here in the initial condition where the top board 2 is horizontal, the distance between the axis C and the floor is equal to the distance between the intersection D and the floor. In addition, the axis C and the intersection D is on a surface of the top board 2 where the subject M is placed.

Figure 6:
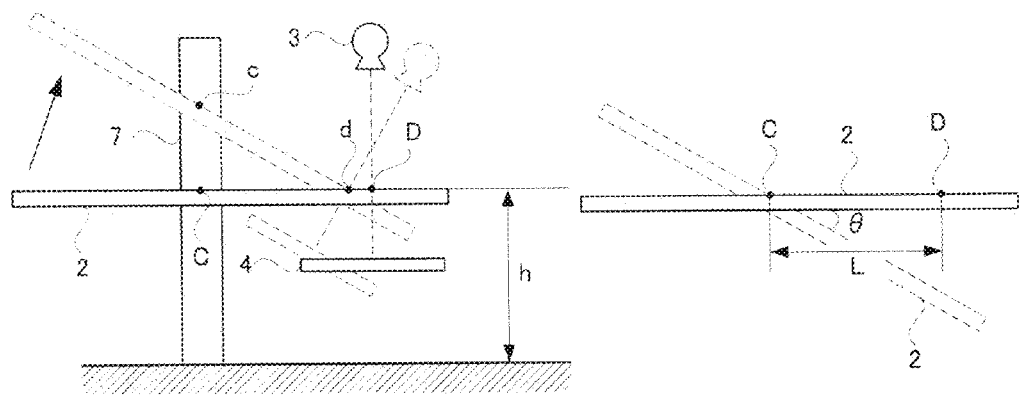

FIG. 6 illustrates on the left thereof how the top board 2 is rotated clockwise. As illustrated on the left of FIG. 6, the top board 2 is moved upward vertically following the rotation of the top board 2. Accordingly, the axis C is moved upward vertically to a position denoted by a numeral c. The intersection D is shifted horizontally to a position denoted by a numeral d. However, the intersection D is not shifted vertically following the horizontal movement thereof. In this manner, the top-board lifting controller 12 controls the top-board lifting mechanism 11 in association with operation of the top-board rotation controller 10 so as for a level of the intersection of the top board 2 and the line connecting the X-ray tube 3 to the FPD 4 to be maintained constant.

The top-board lifting controller 12 operates in association with the top-board rotating mechanism 9 in this manner by successive transmission of signals from the top-board rotating mechanism 9 to the top-board lifting controller 12. Specifically, the top-board rotation controller 10 transmits a signal to the top-board lifting controller 12 for moving the top board 2 upon starting operation of the top-board rotating mechanism 9. Subsequently, a current rotation angle $\theta$ of the top board 2 is transmitted to the top-board lifting controller 12. The top-board lifting controller 12 calculates a moving distance of the top board 2 in the vertical direction in accordance with the rotation angle $\theta$ and a distance H between the axis C and the intersection D, and controls the top-board lifting mechanism 11 based on the rotation angle $\theta$ and the distance H. FIG. 6 schematically illustrates the rotation angle $\theta$ and a distance L on the left thereof. Here, a moving distance is denoted by $L \sin \theta$. In addition, denoting a level of the axis C with the top board 2 in its initial condition by h and denoting a level of the axis C when the top board 2 is rotated by a rotation angle $\theta$ by H, the following relationship is given. Here, the level is a height from the floor of the inspection room.

$$H = h + L \sin \theta$$

The top-board lifting controller 12 controls the top-board lifting mechanism 11 using the above relational expression.

<Operation of Top Board>

Figure 7:
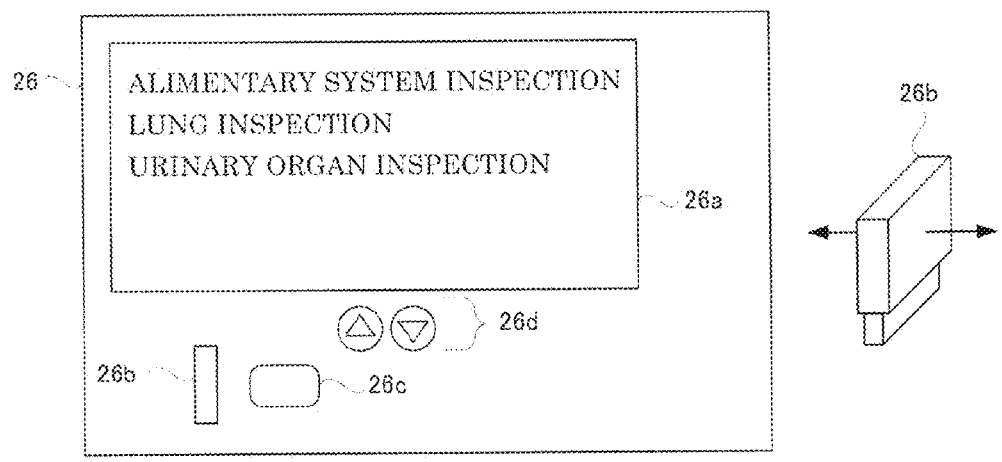
FIG. 7 is a plan view illustrating a console according to the embodiment.
Figure 14:
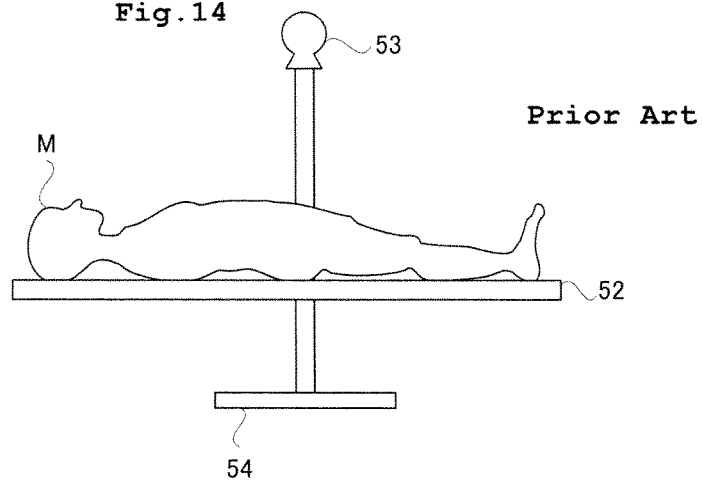
FIGS. 14 to 16 are schematic views each illustrating a currently-used X-ray apparatus.
Figure 15:
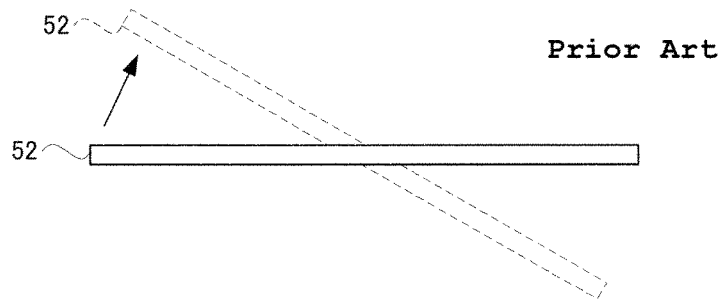
Figure 16:
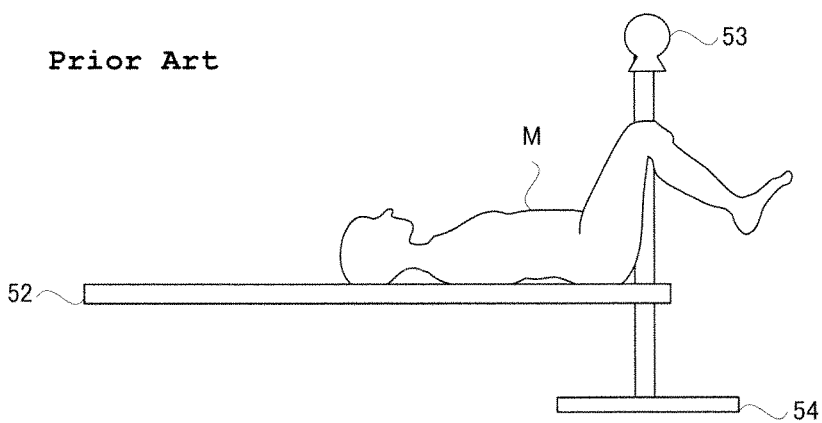

The following describes actual operation of the top board 2. FIG. 7 illustrates on the left thereof the console 26 according to the present invention. Various input devices of the console 26 are to be described.

The console 26 includes an operating panel 26a. The operating panel 26a displays imaging modes each indicating an imaging target. An operator selects one of the imaging modes for transmitting an inspection to be conducted to the apparatus. This achieves setting of parameters for the imaging target at one time by merely selecting the imaging mode without manual input of the parameters concerning the imaging one by one. Examples of the imaging mode displayed on the operating panel 26a include an inspection for urinary organs. The console 26 causes the operator to input the imaging mode.

The console 26 also includes a top board inclining switch 26b. The top board inclining switch 26b causes the operator to input a command about the direction and the extent to which the top board 2 is inclined. As illustrated on the right of FIG. 7, the top board inclining switch 26b allows the operator to input the command by tilting a plate frame rightward/leftward. For instance, when the operator tilts the frame leftward, the top-board rotating mechanism 9 rotates and inclines the top board 2 counterclockwise. When the operator releases his/her hand from the frame, the frame returns to its original position before the inclination of the frame. Accordingly, the top board 2 stops inclination. Similarly, when the operator tilts the frame rightward, the top-board rotating mechanism 9 rotates and inclines the top board 2 clockwise. When the operator releases his/her hand from the frame, the frame returns to its original position before the inclination of the frame. Accordingly, the top board 2 stops inclination.

As noted above, the operator issues no command about rotation of the top board 2 directly to the top-board lifting controller 12. On the other hand, the top-board lifting controller 12 lifts the top board 2 in association with the top-board rotating mechanism 9. Consequently, the level h of the intersection D in FIG. 5 is maintained constant regardless of the inclination of the top board 2.

The console 26 also includes a changeover switch 26c causing the operator to input a command about whether or not the top-board lifting controller 12 is associated with the top-board rotating mechanism 9. Turning on the changeover switch 26c causes the top-board lifting controller 12 to maintain the level h of the intersection D. On the other hand, turning off the changeover switch 26c causes top-board lifting controller 12 not to operate the top-board lifting mechanism 11 regardless of the operation of the top-board rotating mechanism 9. In other words, if the changeover switch 26c is in an off-state, the top board 2 is rotated in a currently-used manner. As noted above, the console 26 includes the changeover switch 26c inputting selection about operation or not operation of the top-board lifting controller 12 in association with the top-board rotation controller 10.

The console 26 further includes an up-down button 26d setting the level h of the intersection D. The up-down button 26d is formed by an up button increasing the level h and a down button decreasing the level h. This allows the operator to change the level h of the intersection D by operating the top-board lifting controller 12.

<Operation of Top-Board Lifting Controller associated with Input of Operating Panel>

The following describes operation of the top-board lifting controller 12 in the present invention in association with input of the operating panel 26a by the operator. FIG. 8 is a table T stored in the memory unit 28. The table T links the imaging modes with set values h of the distance between the floor of the inspection room and the intersection D, or links the imaging modes with set values of a position of the intersection D in the vertical direction (intersection level). If the operator inputs the selection of the imaging mode via the operating panel 26a, a signal representing the selected imaging mode is transmitted to the top-board lifting controller 12. Then, the top-board lifting controller 12 reads out a level h corresponding to the imaging mode selected by the operator with reference to the table T stored in the memory unit 28. For instance, it is assumed that the operator selects an imaging mode about inspection for urinary organs. The selection corresponds to an intersection level h3. Here, the memory unit 28 corresponds to the storing device in the present invention.

If the imaging mode is selected, the top-board lifting controller 12 moves the top board 2 via the top-board lifting mechanism 11 so as for the distance between the floor and the intersection D to be equal to the intersection level h3. FIG. 9 illustrates the movement of the top board 2 at this time.

<Other Components>

The following next describes other components of the X-ray apparatus 1. An X-ray tube controller 6 controls parameters, such as tube current, tube voltage, and an exposure time of the X-ray tube 3. The FPD 4 detects X-rays from the X-ray tube 3 through the subject M, and generates detection signals. The detection signals are transmitted to an image generating section 21 where an image containing a projection image of the subject M is generated.

A display unit 25 displays every image obtained through radiography. The console 26 inputs a command by the operator about starting X-ray emission or movement of the imaging systems 3 and 4 relative to the top board 2. A main controller 27 controls each of the controllers en bloc. The main controller 27 has a CPU, and provides each of the controllers 6, 10, 12, and 14 as well as the image generating section 21 by executing various programs. The above components may be divided into arithmetic units that perform their functions. A memory unit 28 stores all parameters with respect to control of the X-ray apparatus 1 such as the table T and parameters used for image processing.

<Operation of X-Ray Apparatus>

The following describes operation of the X-ray apparatus with reference to FIG. 10. Firstly, the X-ray apparatus operates to place the subject M on the top board 2 (subject placing step S1). At this time, the subject M is placed on one end of the top board 2 in the long-side direction with his/her leg being bent (see FIG. 1). A holder of the top board 2 holds crura of the subject not shown in FIG. 1.

Thereafter, an operator selects an imaging mode via the operating panel 26a (imaging mode selecting step S2). At this time, the top-board lifting controller 12 moves the top board 2 to a level suitable for the imaging mode with reference to the table T. That is, before the top-board rotation controller 10 operates, the top-board lifting controller 12 controls the top-board lifting mechanism 11 so as for an intersection to be shifted vertically to the level inputted by the operator via the console 26 and associated with the imaging mode. Such a condition has been illustrated in FIG. 9. Here, the top board 2 is not inclined but is in a horizontal original condition. Moreover, the operator also allows the imaging systems 3 and 4 to be moved in the long-side direction of the top board 2 via the console 26. The imaging-system moving mechanism 13 performs the movement.

If the operator operates the up-down button 26d of the console 26, the top-board lifting controller 12 lifts the top board 2 in accordance with the input by the operator. This allows the operator to make fine control of the level of the top board 2 (level fine control step S3). After the step, an external instrument such as a catheter is applied to the subject M. The subject M is connected to the external instrument on the floor via a tube.

If the operator operates the top board inclining switch 26b of the console 26, the top board 2 is inclined accordingly (top board inclining step S4). The inclination is made by rotating the top board 2 integrally with the imaging systems 3 and 4 by the top-board rotating mechanism 9. The top board 2 is lifted following the rotation thereof. The lift is made by lifting the top board 2 integrally with the imaging systems 3 and 4 by the top-board lifting mechanism 11. At this time, the level of the intersection D of the top board 2 and the line connecting the imaging systems 3 and 4 is maintained constant.

After the top board 2 is inclined, the operator issues a command via the console 26 to emit radiation. Then, the X-ray tube controller 6 determines a control condition of the X-ray tube 3 by reading out the control condition of the X-ray tube 3 from the memory unit 28 that is suitable for the imaging mode selected by the operator (imaging starting step S5). Thereafter, the X-ray tube 3 emits X-rays to the FPD 4. The FPD 4 detects X-rays passing through the subject M, and outputs detection signals. The image generating section 21 generates a fluoroscopy image based on the detection signals from the FPD 4. The display unit 25 displays the fluoroscopy image. In this manner, an inspection is completed.

In the X-ray apparatus 1 according to the embodiment of the present invention, the top board 2 supporting the subject M placed thereon is rotatable and liftable. The characteristic feature of the embodiment of the present invention is to synchronize lifting and rotation of the top board 2. That is, the level of the intersection D of the top board 2 and the line connecting the X-ray tube 3 to the FPD 4 is controlled to be constant in association with the operation of the top-board rotation controller 10. This achieves a constant level of a region of interest (a site to be imaged) of the subject M regardless of the rotation of the top board 2. Consequently, an invariable distance is obtainable between the subject M and the external instrument on the floor, allowing suppression in pulling of the external instrument due to the vertical movement of the subject M. As a result, the embodiment of the present invention allows provision of a radiographic apparatus with safety and time-saved imaging.

Moreover, an operator inputs selection of operating or not operating the top-board lifting controller 12 in association with the top-board rotation controller 10. This obtains imaging while a moving form of the top board 2 according to the embodiment of the present invention with a maintained level of the intersection D and a currently-used moving form of the top board 2 are selectable freely. Consequently, the above construction allows provision of the X-ray apparatus 1 with a high degree of flexibility for imaging.

Moreover, as in the above construction in which the imaging mode indicating the imaging target is selectable, setting the level of the intersection D is obtainable in association with the specified imaging mode by the operator. This achieves automatic shifting of the intersection D to a level suitable for imaging by merely selection the imaging mode. Consequently, the above construction allows provision of the X-ray apparatus 1 with ease of operation.

The X-ray apparatus 1 according to the embodiment of the present invention is suitable for an inspection for urinary organs. Upon the inspection for urinary organs, the region of interest of the subject M is located at the end of the top board 2 in the long-side direction. Accordingly, rotation of the top board 2 is likely to cause a variation in distance between the floor and the region of interest of the subject M. The embodiment of the present invention achieves a constant level of the region of interest of the subject M. Consequently, a possibly suppressed variation in positional relationship between the subject M and the external instrument is obtainable, and thus the X-ray apparatus 1 with ease for operation can be provided.

The present invention is not limited to the foregoing embodiment, but may be modified as under.

(1) The foregoing embodiment discusses a medical apparatus. The present invention is applicable also to apparatus for industrial use and for the nuclear field.

(2) X-rays used in the foregoing embodiment are one example of radiation in the present invention. Therefore, the present invention may be adapted also for radiation other than X-rays.

(3) Embodiment 1 has no disclosure about a condition when the X-ray tube 3 and the FPD 4 are moved relative to the top board 2 after the changeover switch 26c is turned on. Various aspects are adoptable for the condition. The X-ray tube 3 and the FPD 4 are moved relative to the top board 2 after the changeover switch 26c is turned on, and accordingly the intersection D is shifted. The top-board lifting controller 12 may lift the top board 2 so as for the moving intersection D to be in the constant level.

The following another embodiment is adoptable. That is, the top-board lifting controller 12 stores information on a position of the intersection D when the changeover switch 26c is turned ON, and lifts the top board 2 such that the level of the intersection D is always equal to the level of the original intersection D with the changeover switch 26c being turned ON regardless of the movement of the X-ray tube 3 and the FPD 4 relative to the top board 2. That is, a command is inputted via the console 26 to start associated operation of the top-board lifting controller 12, and then the top-board lifting controller 12 operates to maintain the level of the intersection D to be constant at the time of inputting the commands to start the associated operation. Any embodiments achieve an effect of the present invention.

(4) The top-board lifting controller 12 in Embodiment 1 operates so as for the level of the intersection D on the top board 2 to be always constant. However, the embodiment of the present invention is not limited to this. The top-board lifting controller 12 may lift the top board 2 so as for a level of a point E on the top board 2 to be always constant as illustrated in FIG. 11. With such a construction, the top-board rotation controller 10 rotates the top board 2 in the horizontal state, and accordingly the top-board lifting controller 12 moves the top board 2 vertically. At this time, the top-board rotation controller 10 and the top-board lifting controller 12 shift the point E on the top board 2 to a position denoted by a numeral e located horizontally relative to the point E. However, the point E is not shifted vertically. Consequently, the embodiment is suitable for an X-ray apparatus used for inspection for myeloma.

The X-ray apparatus 1 according to the modification of the present invention allows the operator to select the position of the point E on the top board 2 via the console 26.

Alternatively, the point E may be set automatically. That is, selection of the imaging mode by the operator via the operating panel 26a causes automatic determination of the position of the point E. The operating panel 26a displays the imaging modes as illustrated in FIG. 12 one of which the operator can select. Selecting the imaging mode in this manner allows a significant saving in setting of the radiography condition by the operator. Such a construction has been described on the left of FIG. 7.

With the X-ray apparatus 1 having such a construction, an operator selects one of the imaging modes, and accordingly the top-board lifting controller 12 operates. This is to be described as under. FIG. 13 illustrates a table Ta indicating set values each linking the imaging mode stored in the memory unit 28 with the position of the point E on the top board 2. If the operator inputs selection of the imaging mode via the operating panel 26a, a signal representing the selected imaging mode is transmitted to the top-board lifting controller 12. Then the top-board lifting controller 12 reads out the position of the point E corresponding to the imaging mode selected by the operator with reference to the table Ta stored in the memory unit 28.

If the imaging mode is selected, the top-board lifting controller 12 operates to identify the position of the point E on the top board 2 so as to obtain a constant distance between the floor and the point E. The table Ta may also have a correlationship to a set value of a level of the point E. In this case, if the imaging mode is selected, the top-board lifting controller 12 causes the top-board lifting mechanism 11 to move the top board 2 to a point where a distance between the floor and the point E corresponds to the set value. The operation of the top board 2 at this time is similar to that illustrated in FIG. 9.

INDUSTRIAL APPLICABILITY

As noted above, the present invention is suitable for a radiographic apparatus for medical uses.

REFERENCE SIGN LIST 2 top board
3 X-ray tube (radiation source)
4 FPD (detecting device)
9 top-board rotating mechanism (rotating device)
10 top-board rotation control device (rotation control device)
11 top-board lifting mechanism (lifting device)
12 top-board lifting controller (lifting controller)
13 imaging-system moving mechanism (imaging-system moving device)
14 imaging-system movement controller (imaging-system movement controller)
26 console (input device)
28 memory unit (storing device)

The invention claimed is:

1. A radiographic apparatus comprising:
(A) a radiation source emitting radiation;
(B) a top board supporting a subject placed thereon;
(C) a detecting device detecting radiation passing through the subject;
(D) a rotating device rotating the top board, the radiation source, and the detecting device with a maintained relative positional relationship thereamong, and rotating around a rotary shaft extending in a short-side direction of the top board;
(E) a rotation control device controlling the rotating device;
(F) a lifting device moving the top board, the radiation source, and the detecting device vertically with the maintained relative positional relationship; and
(G1) a lifting controller controlling the lifting device to move the top board, the radiation source, and the detecting device in association with operation of the rotation control device to maintain a level of an intersection of the top board and a line connecting the radiation source to the detecting device constant, wherein
the level indicates a height from a floor on which the radiographic apparatus is placed.

2. The radiographic apparatus according to claim 1, further comprising:
an imaging-system moving device moving the radiation source and the detecting device integrally relative to the top board in a long-side direction of the top board; and
an imaging-system movement controller controlling the imaging-system moving device, wherein
a positional relationship between the rotary shaft and the top board when the rotating device rotates the top board, the radiation source, and the detecting device is invariable regardless of operation of the imaging-system moving device.

3. The radiographic apparatus according to claim 1, further comprising:
(H) an input device inputting selection of operating or not operating the lifting controller in association with the rotation control device.

4. The radiographic apparatus according to claim 3, further comprising:
a storing device storing a table that links an intersection level as a positional set value of the intersection in the vertical direction with an imaging mode indicating an imaging target, wherein
the input device causes an operator to input the imaging mode, and
the lifting controller controls the lifting device, prior to the operation of the rotation, so as for the intersection to be shifted in the vertical direction to a level of the intersection associated with the imaging mode inputted by the input device.

5. The radiographic apparatus according to claim 2, further comprising:
(H) an input device inputting selection of operating or not operating the lifting controller in association with the rotation control device.

6. The radiographic apparatus according to claim 5, wherein
if a command is inputted via the input device for starting association of the lifting controller, the lifting controller operates to maintain the level of the intersection upon the starting association to be constant.

7. The radiographic apparatus according to claim 1 applicable to an inspection for urinary organs.

8. A radiographic apparatus, comprising:
(A) a radiation source emitting radiation;
(B) a top board supporting a subject placed thereon;
(C) a detecting device detecting radiation passing through the subject;
(D) a rotating device rotating the top board, the radiation source, and the detecting device with a maintained relative positional relationship thereamong, and rotating around a rotary shaft extending in a short-side direction of the top board;
(E) a rotation control device controlling the rotating device;
(F) a lifting device moving the top board, the radiation source, and the detecting device vertically with the maintained relative positional relationship; and
(G2) a lifting controller controlling the lifting device to move the top board, the radiation source, and the detecting device in association with operation of the rotation control device so as for a level of a portion on the top board to be maintained constant, wherein the level indicates a height from a floor on which the radiographic apparatus is placed.

9. The radiographic apparatus according to claim 8, further comprising:

an input device inputting selection of the portion on the top board.

10. The radiographic apparatus according to claim 8, further comprising:

a storing device storing a table linking the position of the portion on the top board with the imaging mode indicating the imaging target; and an input device causing the operator to select the imaging mode.

11. The radiographic apparatus according to claim 8 applicable to an inspection for myeloma.

12. A radiographic apparatus comprising:

a radiation source emitting radiation;

a top board on which a subject is placed;

a detecting device detecting radiation passing through the subject;

a rotating device rotating the top board, the radiation source, and the detecting device around a rotary shaft extending in a short-side direction of the top board while maintaining a positional relationship among the top board, the radiation source, and the detecting device;

a lifting device moving the top board, the radiation source, and the detecting device vertically while maintaining the positional relationship among the top board, the radiation source, and the detecting device; and a processor programmed to control the rotating device to rotate the top board, the radiation source, and the detecting device, and the lifting device to move the top board, the radiation source, and the detecting device according to operation of the rotating device to maintain a level of an intersection of the top board and a line connecting the radiation source to the detecting device constant, wherein the level indicates a height from a floor on which the radiographic apparatus is placed.

* * * * *